United States Patent [19]
Montgomery

[11] Patent Number: 5,146,915
[45] Date of Patent: Sep. 15, 1992

[54] ANESTHETIC VAPORIZERS

[75] Inventor: Fredrick J. Montgomery, Bradford, England

[73] Assignee: The BOC Group plc., Windlesham, England

[21] Appl. No.: 638,861

[22] Filed: Jan. 8, 1991

[30] Foreign Application Priority Data

Jan. 9, 1990 [GB] United Kingdom ............... 9000421

[51] Int. Cl.⁵ ............................................ A61M 11/00
[52] U.S. Cl. ........................ 128/203.14; 128/203.12;
128/203.26; 128/203.27; 128/204.14
[58] Field of Search ............... 128/203.26, 203.27,
128/204.14, 203.12, 204.17, 203.25, 203.14

[56]  References Cited
U.S. PATENT DOCUMENTS

| | | | |
|---|---|---|---|
| 3,362,404 | 1/1968 | Beasley | 128/204.14 X |
| 3,528,418 | 9/1970 | Grosholz | 128/204.14 X |
| 3,703,172 | 11/1972 | Hay | 128/188 |
| 3,841,560 | 10/1974 | Sielaff | 239/136 |
| 4,305,888 | 12/1981 | Brisson | 128/204.17 |
| 4,313,436 | 2/1982 | Schwanbom | 128/203.12 |
| 4,611,590 | 9/1986 | Ryschka | 128/203.14 |
| 4,770,168 | 9/1988 | Rusz | 128/203.12 |
| 4,879,997 | 11/1989 | Bickford | 128/200.21 |
| 5,062,999 | 11/1991 | Wallroth | 261/39.1 |

FOREIGN PATENT DOCUMENTS

| | | |
|---|---|---|
| 0348019 | 12/1989 | European Pat. Off. . |
| 2158701 | 5/1973 | Fed. Rep. of Germany ........... 128/203.14 |
| 2840762 | 5/1979 | Fed. Rep. of Germany ........... 128/203.14 |
| 2008359 | 1/1970 | France . |
| 1224478 | 3/1971 | United Kingdom . |
| 1248662 | 10/1971 | United Kingdom ........... 128/203.14 |
| 1299311 | 12/1972 | United Kingdom . |
| 2148721 | 6/1985 | United Kingdom . |
| 2216807 | 10/1989 | United Kingdom . |

Primary Examiner—Edgar S. Burr
Assistant Examiner—Eric P. Raciti
Attorney, Agent, or Firm—Roger M. Rathbun; Larry R. Cassett

[57] ABSTRACT

An anesthetic vaporizer 1 for use particularly with anesthetic agents having a low boiling point comprises an inlet 2 for carrier gas an an outlet 4 for carrier gas and gaseous anesthetic agents. A first passage 6 extends between the inlet 2 and the outlet 4. A flow restrictor 8 is located within the passage 6. A second passage 10 extends between the first passage 6 at a location upstream of the flow restrictor 8 and a regulator 14. The regulator 14 controls the pressure of gaseous anesthetic agent when flowing through a third passage 26 extending from a vaporizing chamber 12 containing anesthetic agent to the first passage 6 at a location downstream of the flow restrictor 8. A flow control valve 28 is located in the third passage 26.

10 Claims, 6 Drawing Sheets

ANESTHETIC VAPORIZERS

BACKGROUND OF THE INVENTION

The present invention relates to anesthetic vaporizers.

UK Patent No 1 224 478, describes an anesthetic vaporizer of the by-pass type in which a carrier gas such as oxygen, air or nitrous oxide is initially divided on entry to the vaporizer between a first stream which is directed towards the sump or vaporizing chamber of the vaporizer to entrain vapor from a volatile liquid anesthetic contained therein; and a second by-pass stream, the first and second streams subsequently recombining prior to leaving the vaporizer for delivery to a patient.

This known vaporizer has been used successfully over a number of years for delivering anesthetic agents such as halothane, trichloroethylene and halogenated ethers including enflurane, fluoroxene, methoxyflurane and isoflurane. All the aforementioned anesthetic agents have a boiling point at atmospheric pressure well above 40° C.

However, a new anesthetic agent has been developed, namely 2-(difluoromethoxy)-1,1,1,2-tetrafluoroethane, which has a boiling point at atmospheric pressure of between 20° and 25° C. This physical characteristic of 2-(difluoromethoxy)-1,1,1,2-tetrafluoroethane renders existing anesthetic vaporizers, unsuitable for delivering said agent to a patient.

OBJECT OF THE INVENTION

It is the object of the present invention to provide an anesthetic vaporizer which is capable of delivering to a patient a predetermined concentration of an anesthetic agent having a boiling point at normal atmospheric pressure of approximately 20° C.

SUMMARY OF THE INVENTION

According to the present invention, an anesthetic vaporizer comprises an inlet for carrier gas, an outlet for carrier gas and gaseous anesthetic agent for delivery to a patient, a first passage extending between the inlet and the outlet in which is located a flow restrictor, a second passage extending between the first passage at a location upstream of the flow restrictor and a regulator, the regulator controlling the pressure of gaseous anesthetic agent when flowing through a third passage extending from a vaporizing chamber containing anesthetic agent to the first passage at a location downstream of the flow restrictor and a flow control valve located in the third passage.

BRIEF DESCRIPTION OF THE DRAWINGS

Embodiments of the invention will now be described, by way of example, reference being made to the Figures of the accompanying diagrammatic drawings in which.

DETAILED DESCRIPTION OF THE INVENTION

Figure 1:
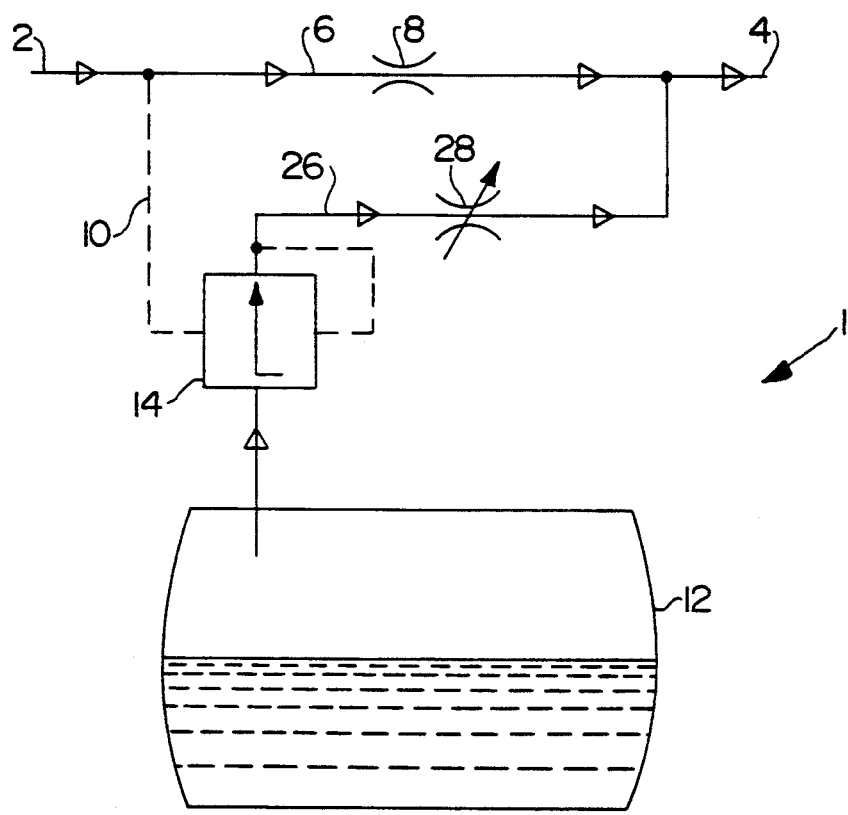
FIG. 1 is a diagrammatic sketch of an anesthetic vaporizer according to the present invention in which are used ISO/BSI symbols.
Figure 2:
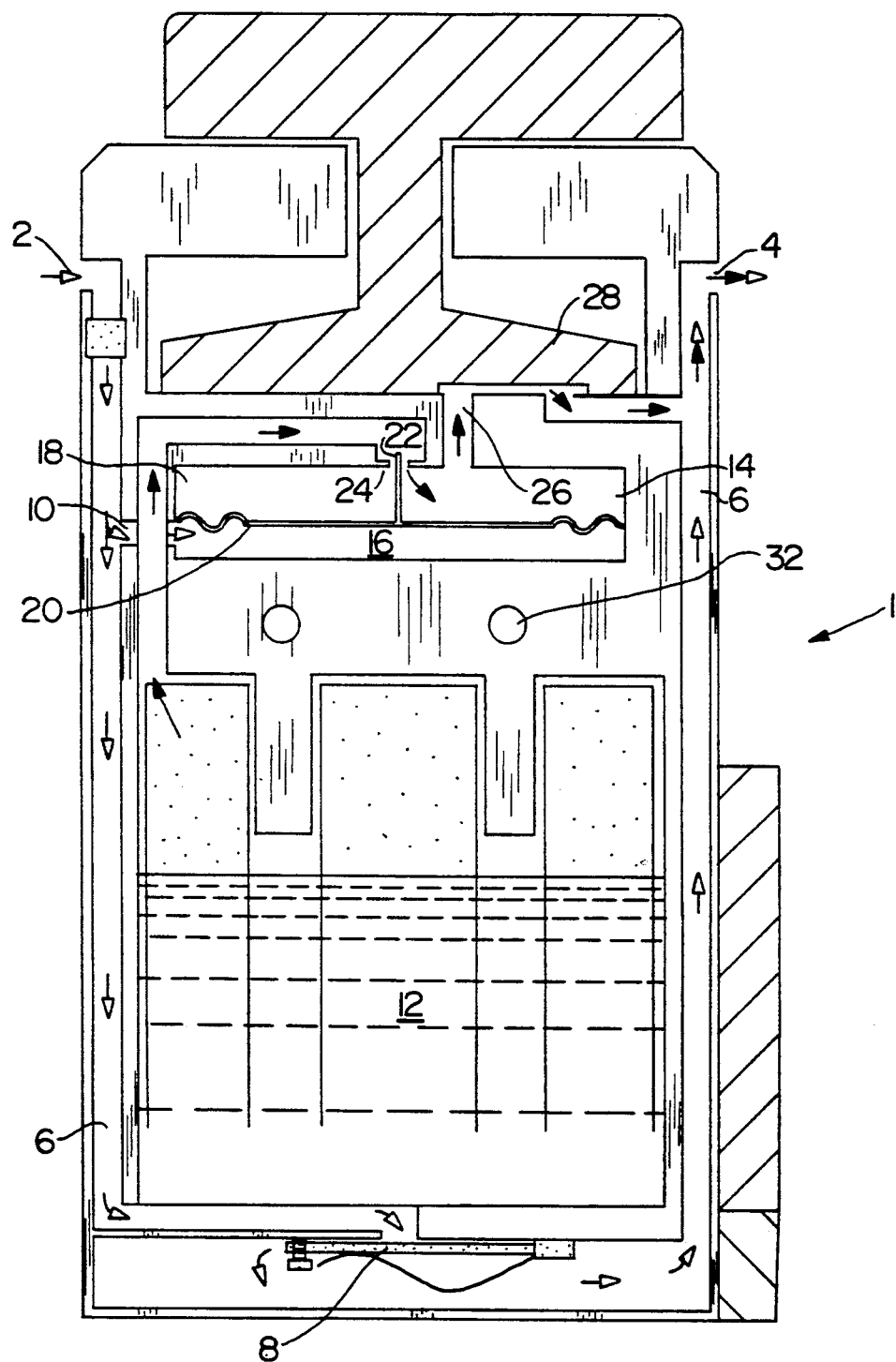
FIG. 2 is a side view partly in cross section of the anesthetic vaporizer of FIG. 1 but with the addition of heaters as illustrated in FIG. 4.

Referring first to FIGS. 1 and 2, an anesthetic vaporizer 1 has an inlet 2 for carrier gas and an outlet 4 for carrier gas and gaseous anesthetic agent. Extending between the inlet 2 and outlet 4 is a passage 6 in which is located a laminar flow by-pass restrictor 8. The restrictor 8 exhibits laminar flow characteristics over its operating flow range.

Extending from a location upstream of the restrictor 8 in the passage 6 is a second passage 10 communicating with a first chamber 16 of a balance regulator 14. The balance regulator 14 includes a second chamber 18 which is separated from the first chamber 16 by diaphragm 20. Connected to the diaphragm 20 for movement therewith is a valve head 22 which co-operates with a valve seat 24. The valve head 22 and valve seat 24 control the flow of gaseous anesthetic agent contained in a vaporizing chamber 12.

Extending from the second chamber 18 is a third passage 26 which extends to the passage 6 downstream of the restrictor 8. A laminar flow control valve 28 is located in the passage 26. The vaporizer 1 includes heaters 32 which are controlled by a temperature sensing device 46. However, the heaters 32 can, in a modification, be controlled by a device for sensing the pressure of anesthetic agent in the vaporizing chamber 12.

In use, energy is supplied to the heaters 32 which converts anesthetic agent from a liquid to a gaseous state which, as shown, is contained in the upper portion of the vaporizing chamber 12. Carrier gas then enters inlet 2 and continues along passage 6 through restrictor 8 towards the outlet 4. The pressure upstream of the restrictor 8 is dependent on the flow rate of carrier gas entering the inlet 2. The pressure in the first chamber 16 of the balance regulator 14 is the same as that upstream of restrictor 8 because of the second passage 10. This causes the diaphragm 20 to move upwards (as shown) taking with it the valve head 22. The valve head 22 will thus separate form the valve seat 24 thereby enabling gaseous anesthetic agent to leave the vaporizing chamber 12 and pass through the second chamber 18 into the passage 26 until the pressure in the passage 27 is the same as that in the chamber 16. The pressure in passage 6 upstream of the restrictor 8 and passage 26 upstream of the control valve 28 are the same. For any position of the control valve 28 the flow rate of gaseous anesthetic agent will depend on that pressure and hence the carrier gas flow rate at the inlet 2. This ensures that the flow of anesthetic agent rises when the carrier gas flow rate rises and vice versa and hence the percentage concentration by volume of the anesthetic agent in the gas delivered to the patient remains constant.

The gaseous anesthetic agent then joins the carrier gas in the passage 6 prior to leaving the vaporizer outlet 4.

As is known in the art and as explained above, the concentration of gaseous anesthetic agent in the carrier gas leaving the outlet 4 is controlled by the setting of the laminar control valve 28.

The profiles of the valve head 22 and the co-operating valve seat 24 are so shaped that at carrier gas flows of up to 15 liters per minute, the pressure of gaseous anesthetic agent in the passage 26 equals the pressure of the carrier gas entering the inlet 2.

Now referring to FIGS. 3 to 6 where like reference numerals denote like features as those described with reference to FIGS. 1 and 2.

Figure 3:
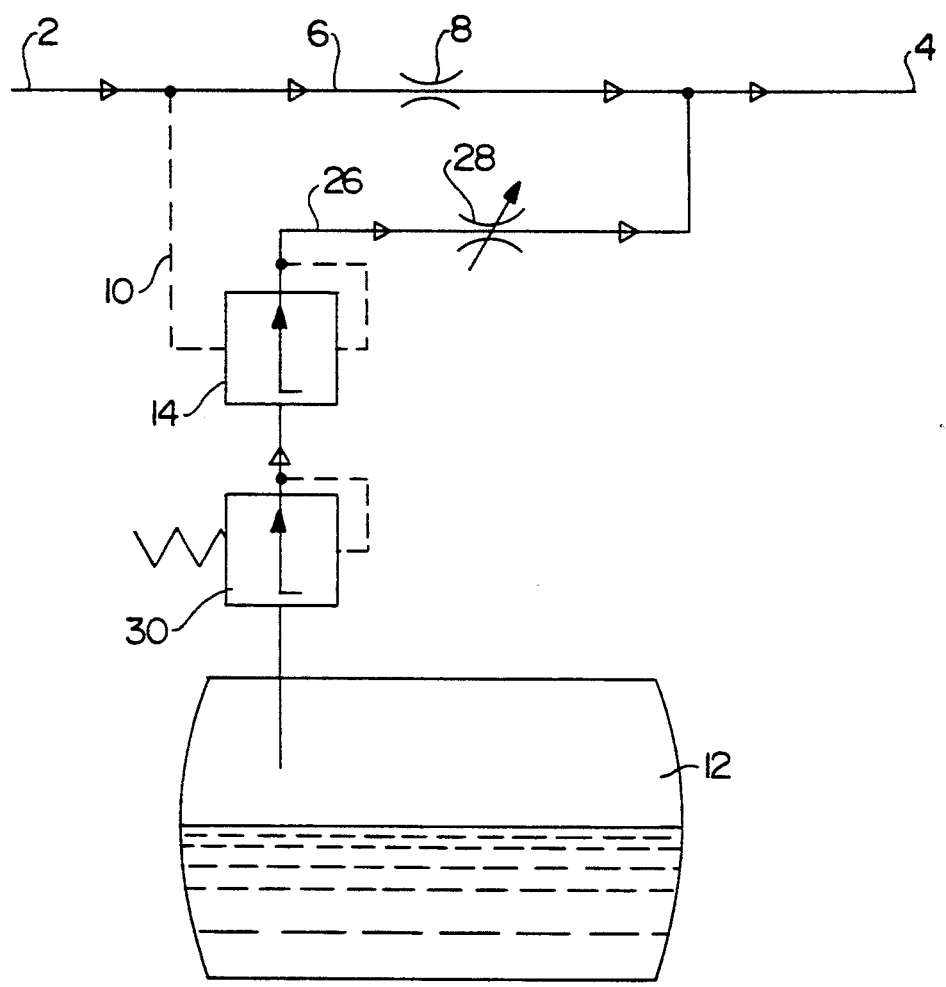
FIG. 3 is a diagrammatic sketch of a modified version of the anesthetic vaporizer of FIG. 1.

Referring in particular to FIG. 3, for very low boiling point anesthetic agents, such as cyclopropane, with a boiling point of minus 32° C. the pressure of the agent in the vaporizing chamber 12 at 22° C. can be very high, on the order of 75 psi. In order to cope with this high pressure a second pressure reducing regulator 30 is located between the vaporizing chamber 12 and the balance regulator 14.

Figure 4:
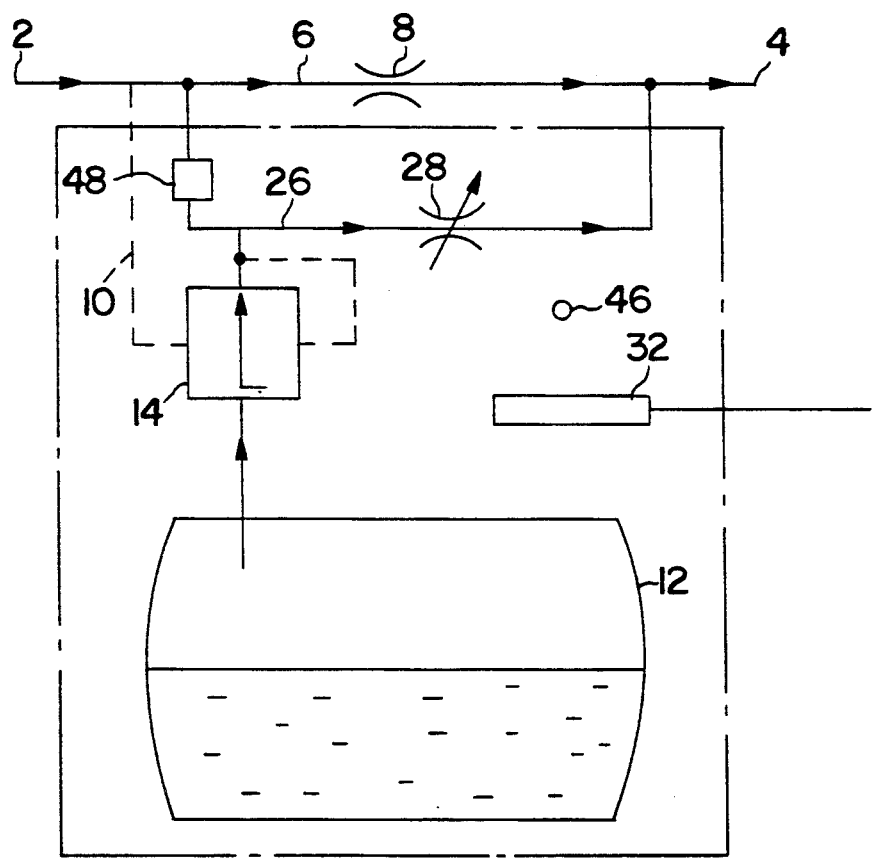
FIG. 4 is a diagrammatic sketch of a further modified anesthetic vaporizer as shown in FIG. 1.

Referring in particular to FIG. 4, when the boiling point of the anesthetic agent is about ambient temperature then to ensure pressure in the vaporizing chamber 12 a heater 32 is provided to raise the temperature of the anesthetic agent to above its boiling point. In the embodiment illustrated in FIG. 4 the heater 32 is positioned within the vaporizer so that, in addition to the vaporizing chamber 12, the passageways 6, 10, 26 and regulator 14 are also heated to prevent the anesthetic condensing out on the walls of the vaporizer which would otherwise be cooler than the vaporizing chamber.

The heater 32 is controlled by a temperature sensing device 46.

Figure 5:
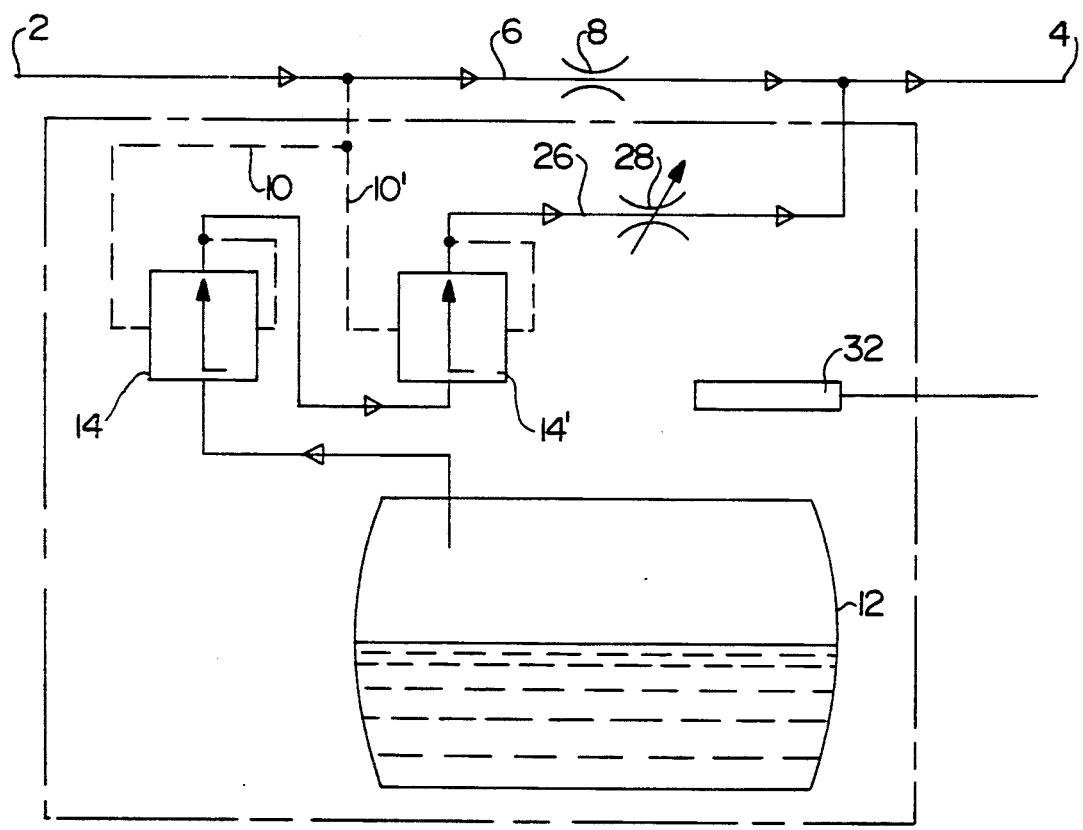
FIG. 5 is a diagrammatic sketch of yet a further modified anesthetic vaporizer as shown in FIG. 1.

In FIG. 5 there is illustrated a modification which provides additional safety in case the regulator 14 should fail in that it provides for a second regulator 14' in series with the regulator 14. As shown, extending from the passage 6 is a passage 10 to the regulator 14 and a separate passage 10' to the regulator 14'.

An alternative safety measure is the provision of a pressure device 48 arranged between the passages 6 and 26 which is arranged to monitor the performance of the regulator 14. The pressure device will automatically detect, for example, a situation where the regulator valve head 22 jams open and higher concentrations of anesthetic agent than those set are being delivered to the outlet 4.

Figure 6:
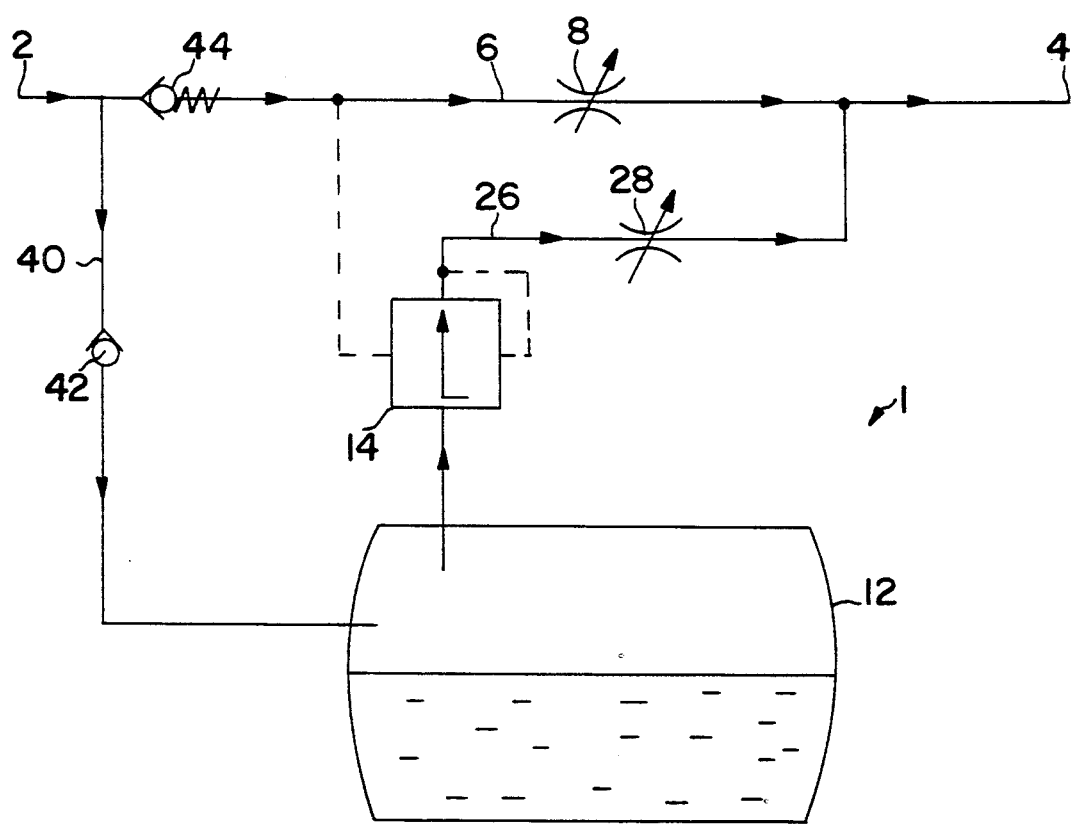
FIG. 6 is a diagrammatic sketch of still a further modification of the anesthetic vaporizer of FIG. 1.

Finally, referring to FIG. 6, the vaporizer 1 includes a by-pass passage 40 extending from the passage 6 adjacent the inlet 2 to the vaporizing chamber 12. A one-way valve 42 is located in the passage 40. Further, a constant back pressure restrictor 44 is located in the passage 6 as shown. When it is necessary to use anesthetic agents whose boiling points are above ambient, for example, above 20° C. within normal operating temperature ranges on the order of 15° C. to 35° C. then, when ambient temperature is above the boiling point, the vaporizer acts as in the embodiment illustrated in FIGS. 1 and 2 with the one-way valve 42 closed. When the ambient temperature is below the boiling point of the anesthetic agent the one-way valve 42 opens and the vaporizer acts as a normal vaporizer of the by-pass type with the laminar flow restrictor 8 being temperature controlled. The laminar flow restrictor 8 thus compensates for changing vapor pressure.

I claim:

1. An anaesthetic vaporizer comprising: an inlet for carrier gas; an outlet for carrier gas and gaseous anaesthetic agent for delivery to a patient; a first passage extending between the inlet and the outlet for flow of carrier gas, and a flow restrictor contained in the first passage; a first regulator; a second passage extending between the first passage at a location upstream of the flow restrictor and the first regulator; a vaporizing chamber containing anaesthetic agent; a third passage extending form said vaporizing chamber to the first passage at a location downstream of said flow restrictor; and a flow control valve contained in the third passage and wherein; the first regulator further including means for controlling the pressure of gaseous anaesthetic agent when flowing through the third passage dependent on the pressure of carrier gas in the first passage upstream of the flow restrictor.

2. An anesthetic vaporizer in accordance with claim 1, wherein the flow restrictor and the flow control valve are substantially laminar flow devices over their operating flow ranges.

3. An anesthetic vaporizer in accordance with claim 1, further comprising a second regulator, the first and second regulators being provided in series.

4. An anesthetic vaporizer in accordance with claim 3, wherein said second regulator is a pressure reducing regulator located between the vaporizing chamber and the first regulator.

5. An anesthetic vaporizer in accordance with claim 1, further comprising a heater located within the anesthetic vaporizer for heating the vaporizing chamber, the first regulator and the flow control valve.

6. An anesthetic vaporizer in accordance with claim 5, wherein said heater is controlled by a temperature sensing device.

7. An anesthetic vaporizer in accordance with claim 5, wherein said heater is controlled by a pressure sensing device which monitors the pressure in the vaporizing chamber.

8. An anaesthetic vaporizer in accordance with claim 5, further comprising a detection device which monitors the operation of the first regulator, and which cuts off power to the heater when it senses a failure of the first regulator.

9. An anesthetic vaporizer in accordance with claim 1, further comprising a detection device which monitors the operation of the first regulator.

10. An anesthetic vaporizer in accordance with claim 1, in which a fourth passage extends between the first passage at a location adjacent the inlet and the interior of the vaporizing chamber, a one-way valve being located in said fourth passage to restrict the flow of carrier gas within the fourth passage to a direction extending from the first passage to the vaporizing chamber.

* * * * *